United States Patent [19]

Harrow

[11] 3,940,439
[45] Feb. 24, 1976

[54] ACID CHLORIDE SYNTHESIS
[75] Inventor: Terence Alfred Harrow, High Wycombe, England
[73] Assignee: G. D. Searle & Co., Chicago, Ill.
[22] Filed: Nov. 14, 1973
[21] Appl. No.: 415,722

[52] U.S. Cl................................. 260/544 Y
[51] Int. Cl.² ................. C07C 51/58; C07C 57/06
[58] Field of Search ........ 260/544 K, 544 Y, 544 M

[56] References Cited
UNITED STATES PATENTS

| | | | |
|---|---|---|---|
| 2,848,491 | 8/1958 | MacKenzie | 260/544 K |
| 3,149,155 | 9/1964 | Seefelder | 260/544 K |

FOREIGN PATENTS OR APPLICATIONS 1,104,995   3/1968   United Kingdom................. 260/544

OTHER PUBLICATIONS

Adams et al. J.A.C.S. Vol. 42 (1920) pp. 599–611.

Primary Examiner—Lorraine A. Weinberger
Assistant Examiner—Richard D. Kelly
Attorney, Agent, or Firm—Barbara L. Cowley

[57] ABSTRACT $\alpha,\beta$-Unsaturated carboxylic acid chlorides are advantageously produced in high yields and with minimal formation of by-products by reaction of the corresponding carboxylic acid with oxalyl chloride.

7 Claims, No Drawings

ACID CHLORIDE SYNTHESIS

The present invention is concerned with a novel method for the manufacture of α,β-unsaturated carboxylic acid chlorides, wherein an α,β-unsaturated carboxylic acid is contacted with oxalyl chloride. The carboxylic acids which may be utilized as starting materials in the process of the present invention are defined by the following structural formula

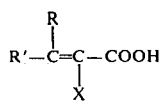

wherein R and R' can be hydrogen or a hydrocarbon, e.g. alkyl, aryl or aralkyl, radical and X is hydrogen, a hydrocarbon or halo radical.

The hydrocarbon radicals encompassed in the foregoing structural formula are exemplified by alkyl radicals such as methyl, ethyl, propyl, butyl, pentyl, hexyl, heptyl and the branched-chain groups corresponding, aryl radicals such as phenyl and tolyl and aralkyl radicals such as benzyl and phenethyl.

The halo radicals denoted above are typified by chloro, bromo, fluoro and iodo.

A preferred embodiment of the present invention comprises the conversion of α-chloroacrylic acid to the corresponding acid chloride by reaction with oxalyl chloride. Previously known methods for the production of this substance have resulted in low yields and also in the formation of large amounts of by-products which render isolation of the desired material most difficult. Thus, when phosgene is used as the chlorinating agent, large quantities of α,β-dichloropropionyl chloride are formed, resulting from the addition of hydrogen chloride across the α,β-unsaturated double bond. This impurity is particularly troublesome by virtue of the fact that it co-distils with the desired acid chloride, thus making isolation of the pure substance most difficult. Other reagents which have been used to effect the production of α-chloroacrylyl chloride from the corresponding acid are benzoyl chloride and thionyl chloride. In both instances, very low yields are obtained.

The discovery that the use of oxalyl chloride in the present process provides high yields of the desired products uncontaminated with troublesome and difficultly separable by-products is most surprising and totally unexpected. Thus, in this process as well as in the method utilizing phosgene as the chlorinating agent, hydrogen chloride is formed as a by-product of the reaction, but only in the case of phosgene is any significant amount of dichloropropionyl chloride produced.

The process of the present invention may be conducted either at room temperature or at elevated temperatures. Mixing of the reactants is preferably carried out at room temperature in order to maintain control of the initial rapid reaction. When that initial reaction has subsided, the mixture can be heated to effect completion of the process. In the interest of economy, equimolar quantities of the reactants are used. Substantially quantitative conversion of the acid to the desired chloride is effected by utilizing an excess amount of oxalyl chloride.

Oxalyl chloride is additionally advantageous over the aforementioned reagents as a result of the fact that it is a liquid, thus does not require the use of a solvent and that it can be heated without loss due to evaporation or decomposition. Phosgene, on the other hand, is a gas, thus is extremely volatile, requires the addition to the reaction mixture of a solvent, thereby increasing the cost of the process. In addition, phosgene is extremely poisonous, thus constitutes a severe safety hazard.

Although the instant process is suitably conducted by allowing the carboxylic acid and oxalyl chloride to interact in the absence of solvents or catalysts, it has been found that the reaction rate is accelerated and the yield improved when a promoter, e.g. an N-substituted carboxylic acid amide such as dimethylformamide or N-methylpyrollidone, is added.

The products of the present process are primarily useful as intermediates in chemical syntheses. Thus, α-chloroacrylyl chloride is a key intermediate in the manufacture of known prostaglandins. These known substances induce a variety of physiological effects, e.g. initiation of labor in a pregnant female mammal. The utilization of that acid chloride as an intermediate is described in detail by Corey et al., *J. Am. Chem. Soc.*, 93, 4326 (1971) and Corey et al., *J. Am. Chem. Soc.*, 91, 5675 (1969). α-Chloroacrylyl chloride is particularly suitable for this reaction in view of the fact that its use results in the formation of the correct stereoisomer.

The invention will appear more fully from the examples which follow. These examples are given by way of illustration only and are not to be construed as limiting the invention either in spirit or in scope as many modifications both in materials and methods will be apparent to those skilled in the art. In these examples temperatures are given in degrees Centigrade (°C.) and quantities of materials in parts by weight unless otherwise noted.

EXAMPLE 1

To 48 parts of α-chloroacrylic acid, at room temperature, is added slowly 58 parts of oxalyl chloride. After the initial rapid reaction has subsided, 1 part of dimethylformamide is added to the stirred mixture and the mixture is heated to 40°, then allowed to cool to room temperature. Distillation of that mixture under reduced pressure affords α-chloroacrylyl chloride, boiling at approximately 45°–48° at 78–80 mm. of pressure.

EXAMPLE 2

The procedure of Example 1 is repeated except that the reactants are allowed to stand at room temperature for approximately 10 minutes before addition of the dimethylformamide. After addition of that promoter the reaction mixture is heated at approximately 35° for about 18 hours, then is subjected to fractional distillation under reduced pressure, in that manner affording the desired product, α-chloroacrylyl chloride boiling at 45°–47.5° under 80 mm. of pressure.

What is claimed is:

1. A process for the manufacture of α-chloroacrylyl chloride which comprises contacting α-chloroacrylic acid with oxalyl chloride and isolating the product.

2. The process of claim 1, wherein the reaction is conducted at room temperature.

3. The process of claim 1, wherein the reaction is conducted at elevated temperature.

4. The process of claim 1, wherein excess oxalyl chloride is used.

5. The process of claim 1, wherein equimolar quantities of α-chloroacrylic acid and oxalyl chloride are used.

6. The process of claim 1, wherein an N-substituted carboxylic acid amide is added to the reaction mixture.

7. The process of claim 1, wherein dimethylformamide is added to the reaction mixture.

* * * * *